(12) United States Patent
Arsenault et al.

(10) Patent No.: US 10,024,808 B2
(45) Date of Patent: Jul. 17, 2018

(54) COLLECTION OF TOMOGRAPHIC INSPECTION DATA USING COMPTON SCATTERING

(71) Applicant: INVERSA SYSTEMS LTD., Fredericton (CA)

(72) Inventors: Paul Arsenault, Fredericton (CA); Shawn Durette, Fredericton (CA); Marc Cabot, Fredericton (CA)

(73) Assignee: INVERSA SYSTEMS LTD., Fredericton (CA)

( * ) Notice: Subject to any disclaimer, the term of this patent is extended or adjusted under 35 U.S.C. 154(b) by 269 days.

(21) Appl. No.: 14/765,542

(22) PCT Filed: Feb. 14, 2014

(86) PCT No.: PCT/CA2014/000110
§ 371 (c)(1),
(2) Date: Aug. 3, 2015

(87) PCT Pub. No.: WO2014/124522
PCT Pub. Date: Aug. 21, 2014

(65) Prior Publication Data
US 2015/0377804 A1    Dec. 31, 2015

Related U.S. Application Data

(60) Provisional application No. 61/765,267, filed on Feb. 15, 2013.

(51) Int. Cl.
*G01J 1/42* (2006.01)
*G01N 23/20066* (2018.01)
*G21K 1/02* (2006.01)
*G01N 23/046* (2018.01)
*G01N 23/203* (2006.01)
*G01N 23/204* (2006.01)

(52) U.S. Cl.
CPC ..... *G01N 23/20066* (2013.01); *G01N 23/046* (2013.01); *G01N 23/203* (2013.01); *G01N 23/204* (2013.01); *G21K 1/02* (2013.01)

(58) Field of Classification Search
CPC .......... G01N 23/046; G01N 23/20066; G01N 23/203; G01N 23/204
USPC ....................................................... 250/393
See application file for complete search history.

(56) References Cited

U.S. PATENT DOCUMENTS

| 7,072,440 B2* | 7/2006 | Mario ................ G01N 23/046 250/367 |
| 7,672,426 B2* | 3/2010 | Seppi ................ G01N 23/046 378/20 |
| 7,965,816 B2 | 6/2011 | Kravis et al. |
| 8,000,436 B2* | 8/2011 | Seppi ................ G01N 23/046 378/19 |

\* cited by examiner

*Primary Examiner* — David Porta
*Assistant Examiner* — Meenakshi Sahu
(74) *Attorney, Agent, or Firm* — Norton Rose Fulbright Canada LLP; Alexandre Daoust (57) ABSTRACT

There is described a method and apparatus for collecting Tomographic inspection data of objects using Compton scatter radiation. The apparatus is of size and weight for portable use within industrial facilities and may be used for assessing integrity of infrastructures in terms of material density, missing materials, thickness of materials, and identification of foreign materials.

19 Claims, 10 Drawing Sheets

COLLECTION OF TOMOGRAPHIC INSPECTION DATA USING COMPTON SCATTERING

CROSS REFERENCE TO RELATED APPLICATION(S)

This application claims all benefit, including priority, of U.S. Provisional Patent Application Ser. No. 61/765,267, filed Feb. 15, 2013, entitled COLLECTION OF TOMOGRAPHIC INSPECTION DATA USING COMPTON SCATTERING, the entire contents of which is incorporated herein by this reference.

TECHNICAL FIELD

The present invention relates to the field of non-destructive inspection using Compton scattered radiation.

BACKGROUND OF THE ART

Infrastructures such as oil refineries, pipes and roadway bridges are managed by use of non-destructive inspection (NDI) and/or non-destructive testing (NDT). By measuring internal integrity, an effective management plan can be produced.

Common modalities used for NDI/NDT include radiography and ultrasonics. Ultrasonic technology is particularly good for such inspections as it provides the ability to obtain quantifiable information such as thickness of components. Radiography is useful for visualization issues and indications of density. However, certain structures pose a challenge for proper NDI, such as insulated vessels. These structures are too thick for radiography and have a barrier (insulation) that prevents the use of ultrasonic technology.

There is therefore a need to provide new NDI/NDT techniques that overcome the aforementioned challenges.

SUMMARY

There is described a method and apparatus for collecting Tomographic inspection data of objects using Compton scatter radiation. The apparatus is of size and weight for portable use within industrial facilities and may be used for assessing integrity of infrastructures in terms of material density, missing materials, thickness of materials, and identification of foreign materials.

Collection of the Tomographic inspection data of objects such as insulated vessels is performed using a radiation source and a detector, each with independent motion along the plane of Tomographic reconstruction adjacent to the object. The radiation source is a pencil beam of radiation particles (i.e. radiation that behaves as a particle), such as gamma-rays, x-rays, and neutrons, emitted into the Tomographic plane of reconstruction through a variety of translated position and rotation angles. The detector also translates and may rotate, and comprises a slit collimator orthogonal to the plane of reconstruction. Behind the detection slit, an array of independent detector sensors may be provided. The apparatus may contain an array of such slits with detector sensors either stacked next to each other or rotated about the line orthogonal to the inspection plane. The intersection between the source beam and field of view of the detector may be rastered throughout the entire inspection plane repeatedly using many different rotation angles of the source beam and the detector. The recorded scattered photons (considering position of acquisition) are then processed numerically to produce a Tomograph of the inspection plane.

In accordance with a first broad aspect, there is provided an apparatus for inspecting an object, the apparatus comprising: a scanning module comprising a source and a detector, the source having an input for receiving radiation particles, a collimator comprising a source aperture for emitting a pencil beam, and a source housing made of a first shielding material for guiding the radiation particles from the input to the source aperture, the detector having at least one detector slit substantially ninety degrees to an imaging plane, at least one detector sensor provided behind each at least one detector slit, and a detector housing made of a second shielding material; and a control module operatively connected to the scanning module and configured to operate the source and detector in the scanning module, and to process signals received by the at least one detector sensor.

In accordance with another broad aspect, there is provided an apparatus for inspecting an object, the apparatus comprising: a scanning module comprising a source and a detector, the source having an input for receiving radiation particles, a collimator comprising a source aperture for emitting a pencil beam, and a source housing made of a first shielding material for guiding the radiation particles from the input to the source aperture, the source housing having a primary shield around the collimator and a secondary shield on each side of the primary shield extending away therefrom, the detector having at least one detector slit, at least one detector sensor provided behind each at least one detector slit, and a detector housing made of a second shielding material; and a control module operatively connected to the scanning module and configured to operate the source and detector in the scanning module, and to process signals received by the at least one detector sensor.

In accordance with yet another broad aspect, there is provided an apparatus for inspecting an object, the apparatus comprising: a scanning module comprising a source and a detector, the source having an input for receiving radiation particles, a collimator comprising a source aperture for emitting a pencil beam, and a source housing made of a first shielding material for guiding the radiation particles from the input to the source aperture, the detector having at least one detector slit, at least one detector sensor provided behind each at least one detector slit, and a detector housing made of a second shielding material; a retention system inside the scanning module for the source and the detector and allowing coordinated and independent movement thereof; and a control module operatively connected to the scanning module and configured to operate the source and the detector in the scanning module, and to process signals received by the at least one detector sensor.

In accordance with another broad aspect, there is provided an apparatus for inspecting an object, the apparatus comprising: a scanning module comprising a source and a detector, the source having an input for receiving radiation particles, a collimator comprising a source aperture for emitting a pencil beam, and a source housing made of a first shielding material for guiding the radiation particles from the input to the source aperture, the detector having at least one detector slit, at least one detector sensor provided behind each at least one detector slit, and a detector housing made of a second shielding material; and a control module operatively connected to the scanning module, configured to operate the source and the detector in the scanning module and to process signals received by the at least one detector sensor, and comprising a control unit and a signal processing unit, the signal processing unit adapted to display low quality raw data on a user interface in a rapid scan mode and high quality raw data on the user interface in a high quality mode.

In accordance with yet another broad aspect, there is provided an apparatus for inspecting an object, the apparatus comprising: a scanning module comprising a source and a detector, the source having an input for receiving radiation particles, a collimator comprising a source aperture for emitting a pencil beam, and a source housing made of a first shielding material for guiding the radiation particles from the input to the source aperture, the detector having at least one detector slit, at least one detector sensor provided behind each at least one detector slit, and a detector housing made of a second shielding material; and a control module operatively connected to the scanning module by a flexible and releasable cable and configured to operate the source and detector in the scanning module, and to process signals received by the at least one detector sensor.

In accordance with an aspect of the present invention, there is provided a method for collecting Tomographic inspection data of objects using Compton scatter radiation using a scanning module comprising a source and a detector, the method comprising: receiving radiation particles at an input of the source; emitting a pencil beam via a source aperture of a collimator of the scanning module; guiding the radiation particles from the input to the source aperture at least partly by a source housing of the scanning module, the source housing made of a first shielding material; and a control module operatively connected to the scanning module processing signals received by at least one detector sensor of the detector, wherein the detector comprises at least one detector slit extending substantially orthogonally to an imaging plane, the at least one detector sensor provided behind each at least one detector slit, and a detector housing made of a second shielding material.

For the purposes of the present description, the term "detector" will be understood to refer to a detection unit having a housing and comprising a plurality of components. The terms "sensor" and "detector sensor" will be understood to refer to a component inside the detection unit for measuring reflected radiation, i.e. for taking a detection measurement. A detector may thus have one or more sensors provided therein. A sensor may have one or more components therein, such as a detecting crystal (or scintillator).

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

Further features and advantages of the present invention will become apparent from the following detailed description, taken in combination with the appended drawings, in which:

FIG. 4b illustrates a cross-sectional view along the line C-C of FIG. 4a;

It will be noted that throughout the appended drawings, like features are identified by like reference numerals.

DETAILED DESCRIPTION

Figure 1A:
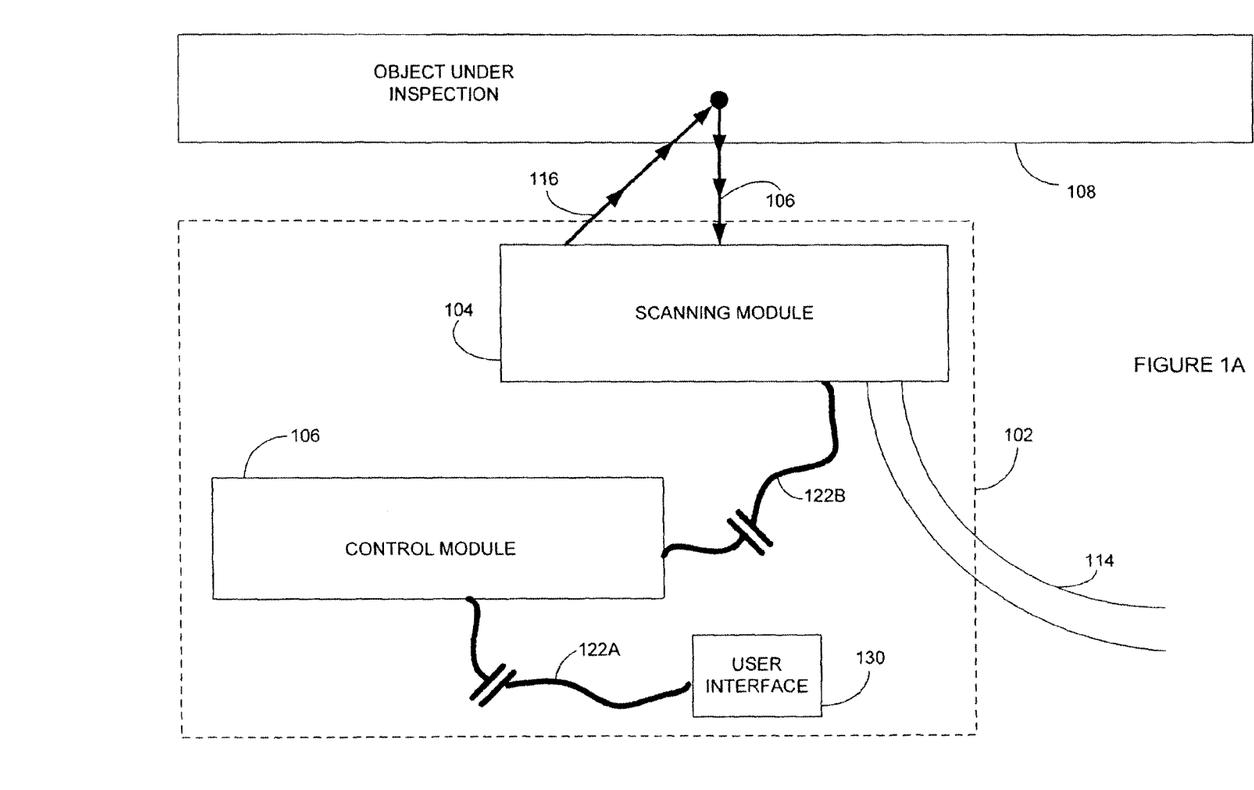
FIG. 1a illustrates an exemplary apparatus for inspecting an object, the apparatus comprising a scanning module and a control module.

Referring to FIG. 1a, there is illustrated an exemplary inspection apparatus 102 for generating Tomographic images of an object under inspection 108. The apparatus 102 is placed adjacent to the object under inspection 108, such as an infrastructure, a wall, a bridge, a road, a pipe, an oil tank, and other types of structures. A source beam of radiation particles 116 is projected onto the object under inspection 108. Back-scattered photons 106, also known as Compton scatter radiation, are collected in order to create the Tomograph along an inspection plane. Single-side access is provided by the Compton scatter effect, as photons enter and emerge from the object under inspection 108 from a same side. The Compton scatter radiation can pass through air gaps and allows inspection through materials such as insulation, fiberglass, and concrete. Inspection may be made through thin layers of ferrous metal or water. An in-plane spatial map of density of an object may thus be generated to assess integrity in terms of material density, missing materials, thickness of materials, and identification of foreign materials.

The apparatus 102 is configured to raster an inspection plane with a small volume of interaction between the source beam 116 and a detector field of view, collecting a statistically meaningful number of photons while maintaining a practical size, weight and speed. The apparatus 102 is composed of three main components, namely a scanning module 104, a control module 106, and a user interface 130. In some embodiments, the control module 106 and the user interface 130 may be integrated into a single component. FIG. 1a illustrates them as separate components connected by a connection means 122a, such as a flexible cable, a rigid cable, an optical fiber, and a wireless connection. The cable 122a may be of varying length, and a particularly long cable allows the user manipulating the user interface 130 to stand at a safe distance from the control module 106 and/or the scanning module 104. The wireless connection may be implemented using various technologies/standards, such as Bluetooth, Infrared, ZigBee, WiFi, WiMax, etc. Data may be transmitted between the user interface 130 and the control module 106 using various types of networks, such as wireless Personal Area Networks (PAN), Local Area Networks (LAN), mesh networks, and a cellular or mobile networks.

The scanning module 104 and control module 106 are connected by a connection means 122b, such as a flexible cable, a rigid cable, an optical fiber, and a wireless connection. Connection means 122b may be the same or different from connection means 122a. In the case of a wired connection, the cable may be detachable from a single end or from both ends. Various connecting devices may be used. In some embodiments, cable portions may extend from both the scanning module 104 and the control module 106 and may be joined together to form a connection using a quick-connect type connector. This allows the user to grip both cable portions at once and makes it easier to line up the two for connection. The cable portion extending from the scanning module 104 and/or the control module 106 may extend from a side or from the back of the module. Having the control module 106 decoupled from the scanning module 104 reduces the size and weight of the scanning module 104, thus allowing better access in tight spaces and easier positioning by the user. The heavier and bulkier components, such as a processor and a power supply, are provided in the control module 106.

The radioactive isotopes used to generate the radiation particles may be provided externally to the apparatus 102 and input thereto via a hose 114 or other isotope carrying device. The apparatus 102 may be designed to accept radiation isotopes employed by service providers for radiography or other purposes. The apparatus 102 may thus be sold and/or transported without the presence of radiation isotopes, thereby reducing costs and increasing safety.

Figure 1B:
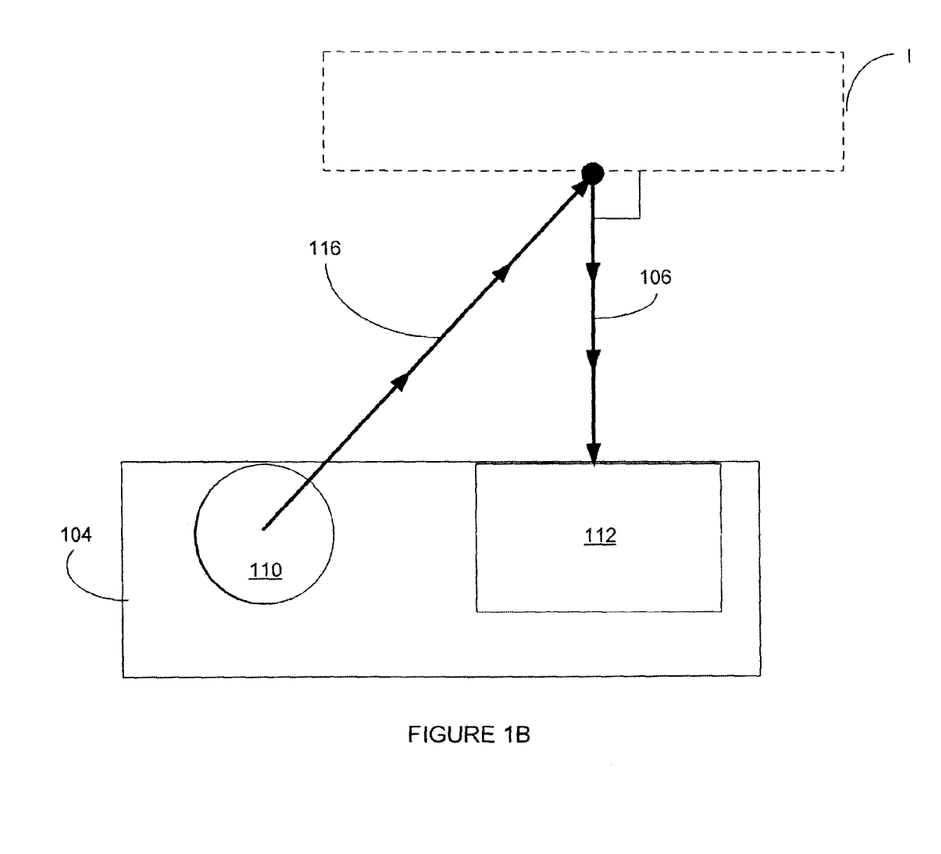
FIG. 1b illustrates an exemplary scanning module of the inspection apparatus.

Turning now to FIG. 1b, there is illustrated an exemplary embodiment for the scanning module 104. A source 110 is mounted within the scanning module 104 and emits the source beam 116 while a detector 112 collects the backscatter photons 106 at a substantially 90° angle to the imaging plane "I".

Figure 2A:
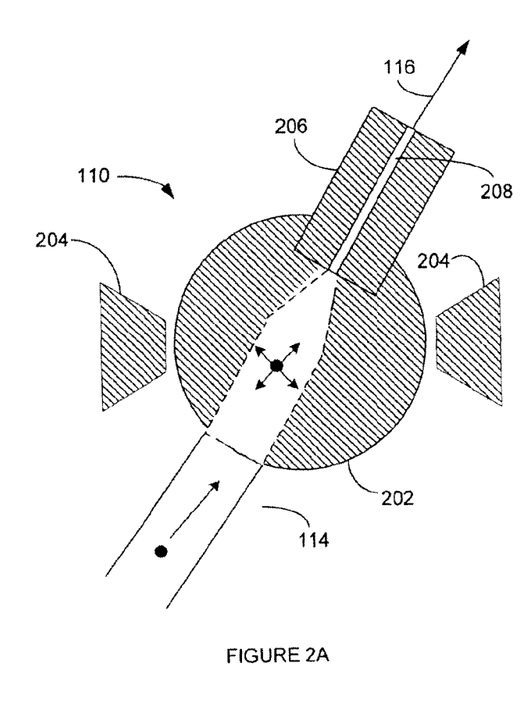
FIG. 2a illustrates a cross-sectional top view of an exemplary source of the inspection apparatus.
Figure 2B:
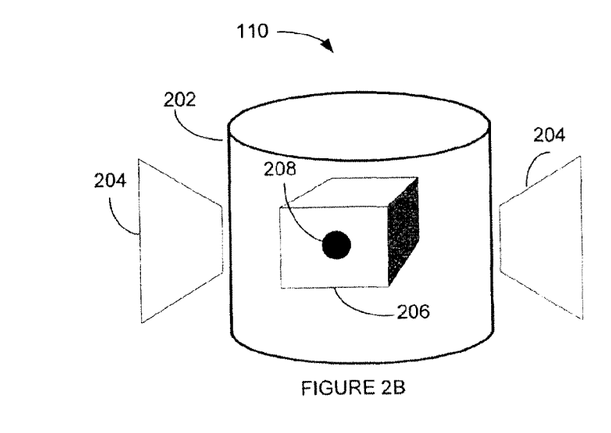
FIG. 2b illustrates a front view of the exemplary source of the inspection apparatus.
Figure 2C:
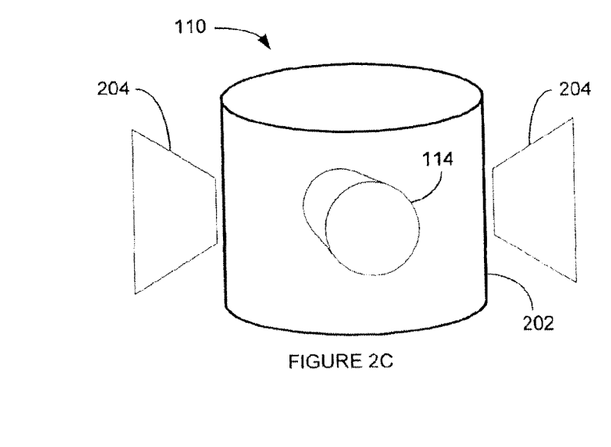
FIG. 2c illustrates a back view of the exemplary source of the inspection apparatus.

A more detailed example of the source 110 is illustrated in FIGS. 2a to 2c. The source beam 116 is a pencil beam emitted from a collimator 206 having an aperture 208. The collimator 206 may be rectangular-shaped, as illustrated, cylindrically shaped, or have an alternative geometry. The collimator 206 may be interchangeable with other collimators having different aperture sizes, thus allowing customization of speed versus resolution based on a desired inspection.

A source housing 202 is made from a shielding material, such as tungsten, lead, or depleted uranium, in order to shield surrounding areas from radiation and guide the radiation into a controlled beam. In some embodiments, the source housing 202 is symmetric about an axis of rotation of the source 110. This provides a constant rate of leakage through the shielding material as the source beam rotates. This also assists with subtracting the level of photons that leak directly to the detector 112 since the leakage rate does not change with rotation angle. The source housing 202 is intended to reduce the emission of photons by the source 110 other than through aperture 208, as a form of leakage.

In some embodiments, the source housing 202 acts as a primary shield, and a secondary shield 204 is provided on each side of the primary shield. The secondary shields 204 may be fixed and serve to reduce leakage from the source 110 directly to the detector 112 without scattering. The shape is designed to block photons with a direct line of sight between the source 110 and the detector 112. Since the radiation source is smaller than the detection volume, having extra shielding close to the source, reduces the needed volume of shielding and thus reduces the weight of the scanning module 104. FIG. 2b is a front view of the source 110, showing the collimator 206 extending from the source housing 202 and a source aperture 208 for emitting the pencil beam (i.e. a cone beam approximating a pencil beam). FIG. 2c is a back view of the source 110, showing the hose 114 protruding from the back side of the source housing 202.

Figure 3A:
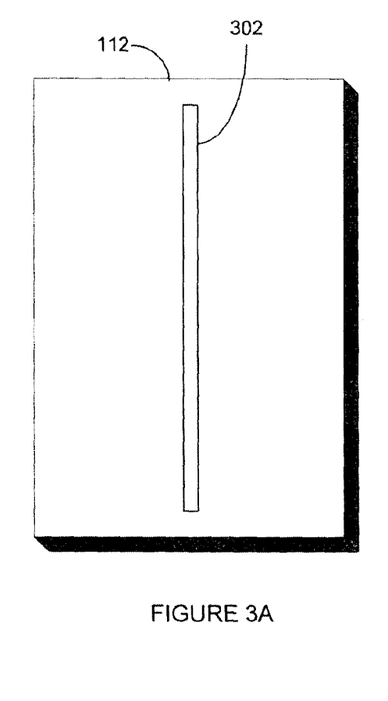
FIG. 3a illustrates a front view of an exemplary detector having a slit with field of view orthogonal to an imaging plane and 90% to front line of imaging plan.
Figure 3B:
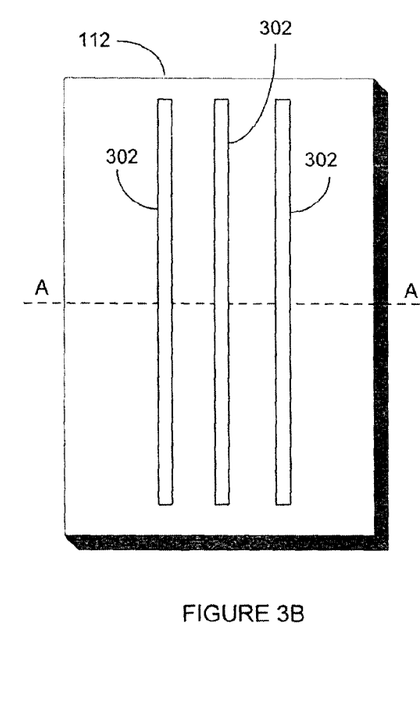
FIG. 3b illustrates a front view of an exemplary detector having an array of slits 90° to the imaging plane.
Figure 3C:
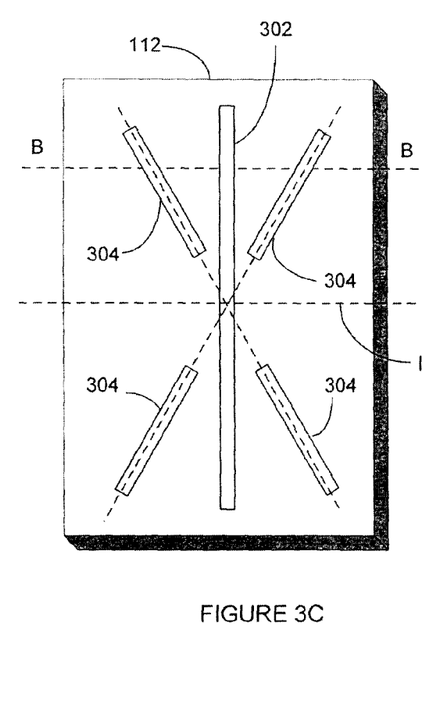
FIG. 3c illustrates a front view of an exemplary detector having additional slits offset from the primary slit 90° from the imaging plane.

Referring to FIGS. 3a-3c, there are illustrated various embodiments for the detector 112. FIG. 3a illustrates a first embodiment, whereby a single slit 302 extends vertically along the front side of the detector 112. The detector slit 302 has a field of view orthogonal to an imaging plane while facing the object being scanned such that the shortest exiting path out of the object is captured, leading to maximum inspection depth. This maximizes the collection of meaningful photons scattered from a small volume, in order to acquire a statistically meaningful measurement from a small region of intersection between the source beam 116 and the detector's 112 field of view. Performing detection along the length of the slit 302 provides more counted photons for a small region of interaction, resulting in increased resolution and tally statistics.

In an alternative embodiment, illustrated in FIG. 3b, an array of slits 302 are provided on the detector 112. Each slit 302 is substantially 90 degrees with respect to the imaging plane and may target a different region of the source beam, speeding up acquisition by interrogating different regions in parallel. The adjacent slits 302 may be of a same length or different length and/or of a same width or different width.

Another alternative embodiment is illustrated in FIG. 3c. In addition to the primary slit 302 positioned substantially 90 degrees to the imaging plane, at least one secondary slit 304 is offset from the primary slit and positioned to receive scattered photons from a same point of origin as those received by the primary slit 302 for all rotations of the source beam. In the example illustrated, four secondary slits 304 are provided, each one approximately 30 degrees offset from a top or bottom end of the primary slit 302, clockwise and counterclockwise, such that if two imaginary lines were traced along a diagonal for each pair of secondary slits 304, they would intersect at a single point that is also along the imaging plane I. The secondary slits 304 may be positioned anywhere in the range of 90° to approximately 45° from the primary slit 302. More than one secondary slit 304 may be provided in each quadrant of the detector face, and they may be of varying lengths and/or widths. Thus, the same region is targeted by all slits 302, 304. This allows the results of all individual detector sensors provided behind each slit 302, 304 to be summed, eliminating the need to calibrate each individual detector sensor. In addition, each slit 302, 304 targets the same scatter region, but has a different exit path. The detector sensors between the slits can be compared and differences between detector sensors in different slits may provide information about the differences in material between the exiting paths. This information may then be used to correct for out of imaging plane features.

Figure 4A:
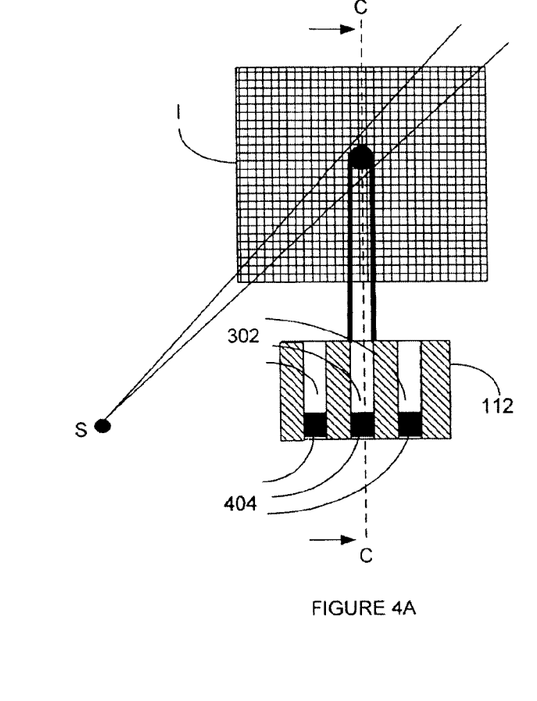
FIG. 4a illustrates a cross-sectional view along the line A-A of FIG. 3b.
Figure 4B:
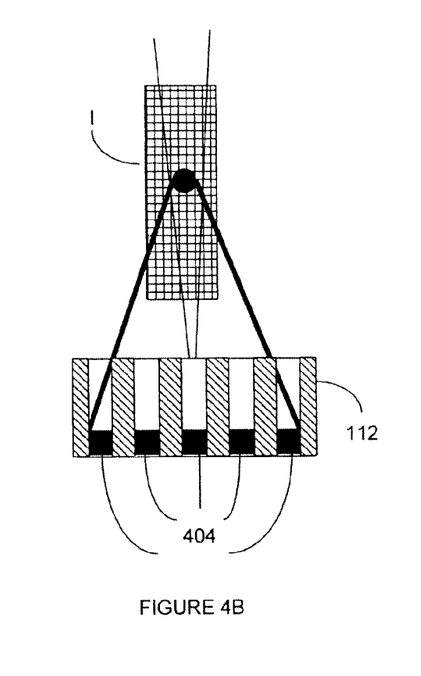

FIG. 4a is a cross-sectional view of the detector 112 and an imaging plane "I" along lines A-A of FIG. 3b. Each slit 302 comprises at least one detector sensor 404. The detector sensor 404 may have the same width as the slit 302. In some embodiments, the ratio of the width of the sensor 404 to the width of the slit 302 is 2:1. Other ratios may also be used. In some exemplary embodiments, the dimensions for the slit 302 and detector sensor 404 are between about 0.25 mm and 1.5 mm in width and between about 40 mm and 160 mm in height. Alternatively, the detector sensors 404 may be larger than or narrower than the slits 302. In some embodiments, each slit 302 comprises an array of detector sensors 404, as illustrated in FIG. 4b which represents a cross-sectional view of FIG. 4a along lines C-C. The array of detector sensors 404 is positioned in the same field of view of the same small region of the pencil beam and thus provides more counted photons for this region. A challenge for the design of the apparatus 102 is that material outside of the imaging plane but still in the field of view of the detector 112 may modulate the recorded scattered Compton photons. On the whole, however, small out of plane features may be averaged out due to the significant volume of detection. Having many detector sensors 404 within each slit 302 allows for some correction of these out of imaging plane features. Each detector sensor 404 can be compared, and detector sensors 404 with outlier tallies can be omitted or have a weighted/reduced contribution to the slit's total tally of measured photons.

Figure 4C:
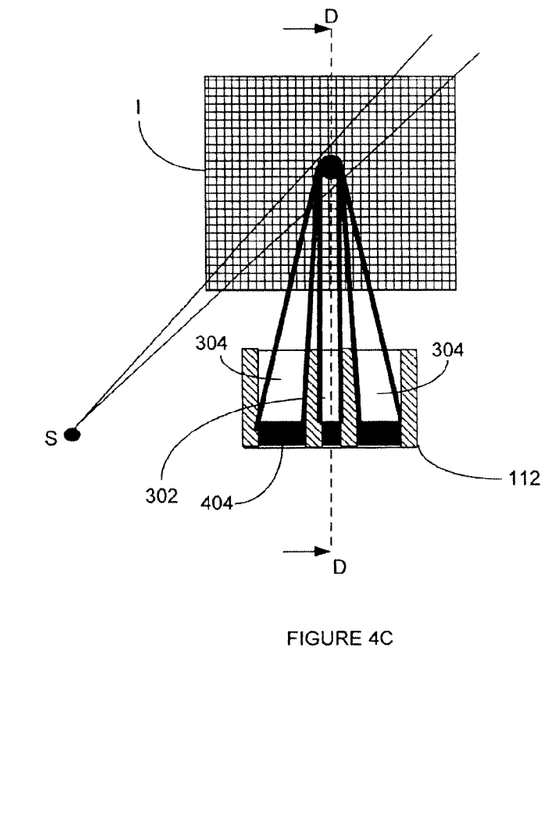
FIG. 4c illustrates a cross-sectional view along the line B-B of FIG. 3c.
Figure 4D:
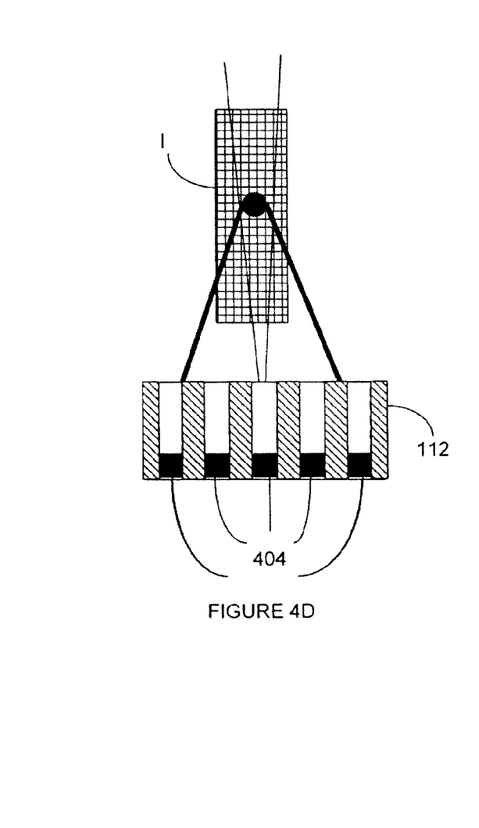
FIG. 4d illustrates a cross-sectional view along the line D-D of FIG. 4c.

Referring to FIG. 4c, there is illustrated a cross-sectional view of the detector 112 and imaging plane I along lines B-B of FIG. 3c. In this embodiment, the primary slit 302 and secondary slits 304 are shown to receive photons from a same region of the imaging plane. As per the cross-sectional view along lines D-D and shown in FIG. 4d, each slit may comprise a column or array of detector sensors 404.

Figure 5A:
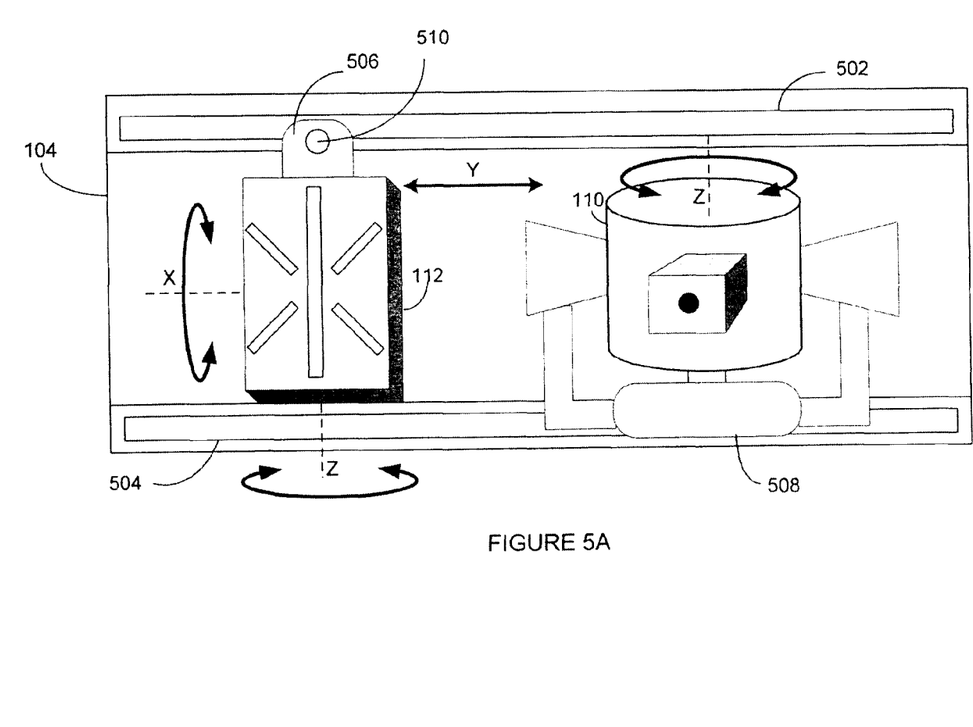
FIG. 5a is an inside front view of an exemplary scanning module.
Figure 5B:
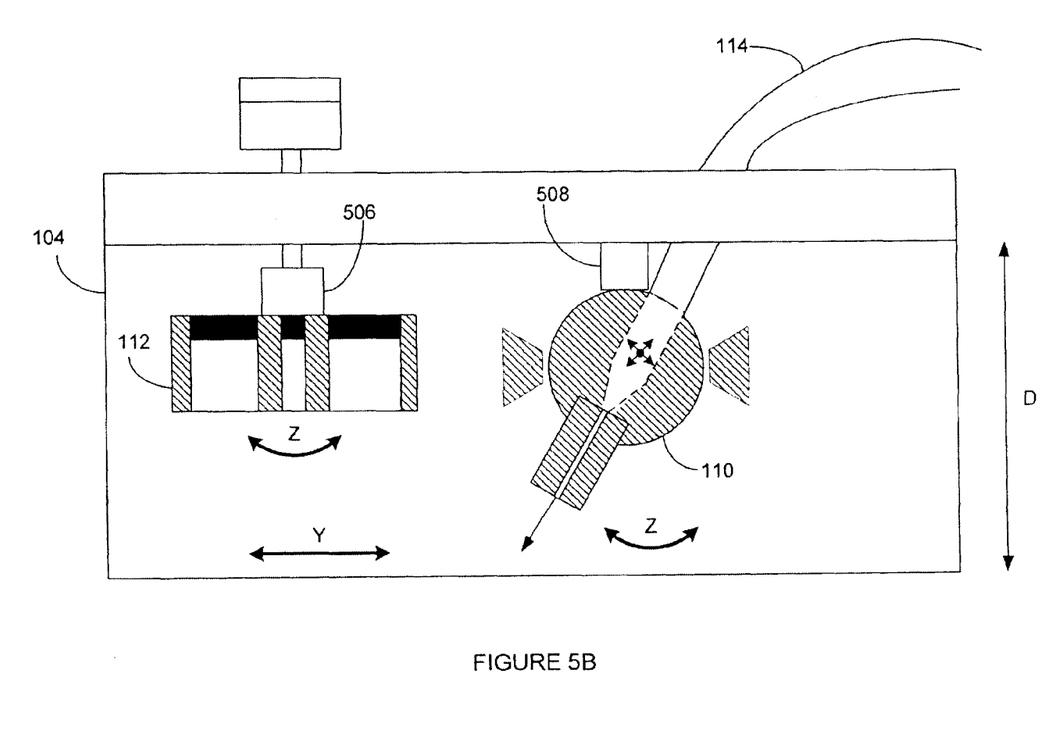
FIG. 5b is an inside top view of an exemplary scanning module.

Turning now to FIGS. 5a and 5b, an exemplary embodiment of the mechanics provided inside the scanning module 104 is illustrated. In some embodiments, the source 110 and detector 112 are held within a retention system that provides translational and rotational motion for one or both of the devices 110, 112. The motion may be automated to follow a specific pattern or manual as dictated by a user of the apparatus 102. This allows selective positioning of the source beam and detector field of view. The source 110 and detector 112 may be moved in a coordinated manner to scan the entire inspection plane. In some embodiments, the source 110 and detector 112 may translate in unison, with a fixed rotation angle, across the inspection area in sweeps. This minimizes stopping and starting of each device 110, 112 and reduces acquisition time. A first sweep may target a region of the inspection area closest to the apparatus 102 and then progressively target deeper regions by rotating the source 110 or detector 112. Deeper regions may also be reached by increasing a separation distance between the source 110 and the detector 112.

The apparatus 102 may produce tallies over known or predetermined counting intervals, such as seconds, milliseconds, nanoseconds, etc. The position of the source 110 and detector 112 may also be recorded and associated to each tally. An average location of the source 110 and detector 112 may be calculated during a tally for Tomographic image reconstruction. During acquisition, the speed of motion may be adjusted to achieve acceptable statistical uncertainty of each tally. Alternatively, a given motion may repeated over a same area until acceptable tally statistics are obtained. Each region of the inspection plane may be targeted several times with different beam angles for the source 110 and/or detector 112. This provides independent information for each region and aids Tomographic reconstruction.

An overpass mechanism may be built into the retention system of the scanning module 104 to allow the source 110 to pass beneath the detector 112, changing the side of the source 110 relative to the detector 112. Additional independent measurements may thus be acquired, aiding in Tomographic image reconstruction and mitigating the effect of source beam modulation by features outside the region of intersection. For certain types of beam geometry, the overpass eliminates the need for a detector 112 on each side of the source 110. The size of the scanning module 104 is also reduced since the detector 112 can be located at either end of a linear actuator during acquisition, maximizing the length of acquisition for a particular length of linear actuators.

As illustrated in FIG. 5a, the detector 112 may be mounted to an upper track 502 and held in place via an attachment device 506 allowing translational movement along direction Y. Similarly, the source 110 may be mounted to a lower track 504 and held in place via another attachment device 508 for translational movement along direction Y. Alternatively, the detector 112 may be mounted to the lower track 504 while the source 110 is mounted to the upper track 502. Also alternatively, both tracks 502 and 504 may be upper or lower tracks, with one provided towards the front of the module 104 and the other provided towards the back of the module 104. In some embodiments, upper track 502 is provided towards the front or back of the scanning module 104 while lower track 504 is provided towards the opposite side, i.e. upper track 502 is provided towards the front while lower track 504 is provided towards the back or vice versa. Sufficient depth D (see FIG. 5b) for the scanning module 104 may thus allow the detector 112 and source 110 to move from one end of the module 104 to the other without obstruction.

In some embodiments, the detector 112 and source 110 are placed inline in terms of translation in order to reduce required shielding. This allows the detector housing to shield the entire detector 112 and minimizes the volume of shielding needed, thus reducing device weight. Thus, a small volume of shielding material can shield all detector sensors in an array. In this case, the attachment device 506 allows movement of the detector 112 about axis X via rotation point 510 such that the source 110 may translate unobstructed along the length of the scanning module 104. In some embodiments, attachment device 508 may also allow rotational movement of the source 110 about axis Z. Part of attachment device 508 may comprise a rotation table which is in turn mounted to the lower track 504. This allows the source beam to target any region of the inspection area from a variety of angles. In some embodiments, attachment device 506 may also allow rotational movement of the detector 112 about axis Z. Part of attachment device 506 may comprise a rotation table which is in turn mounted to the upper track 502. This allows the field of view of the detector 112 to both translate and rotate within the inspection plane.

The source 110 and detector 112 are attached to each other with rigidity and precision via the retention system. This ensures that an encoded beam location for each tally matches an actual acquisition, for the reconstruction process. Precision of the retention system allows better reconstruction of the images by a reconstruction software.

The retention system may be held within a frame or chassis less rigid than the retention system itself. Consequently when the apparatus 102 receives impact or a minor collision, the chassis may be bent, but the automation maintains alignment. Also, the chassis may be designed to serve as a handle for carrying the apparatus 102, or may have attachment points for rope access delivery of the apparatus 102 at great heights. On the top and/or bottom of the chassis (the side in line with the imaging), there may be ruled scales showing the location of the imaging plane which matches positioning information of the automation. This allows the operator to better position the scanning module 104 since the operator's view of the scanned object may be blocked. Ruled scales may be provided on only one or multiple ones of edges adjacent to the scanned object. The ruled scales also allow an easier correlation between a reconstructed image and an actual location of a found defect on site when using a reference point of the scanner location.

Figure 6:
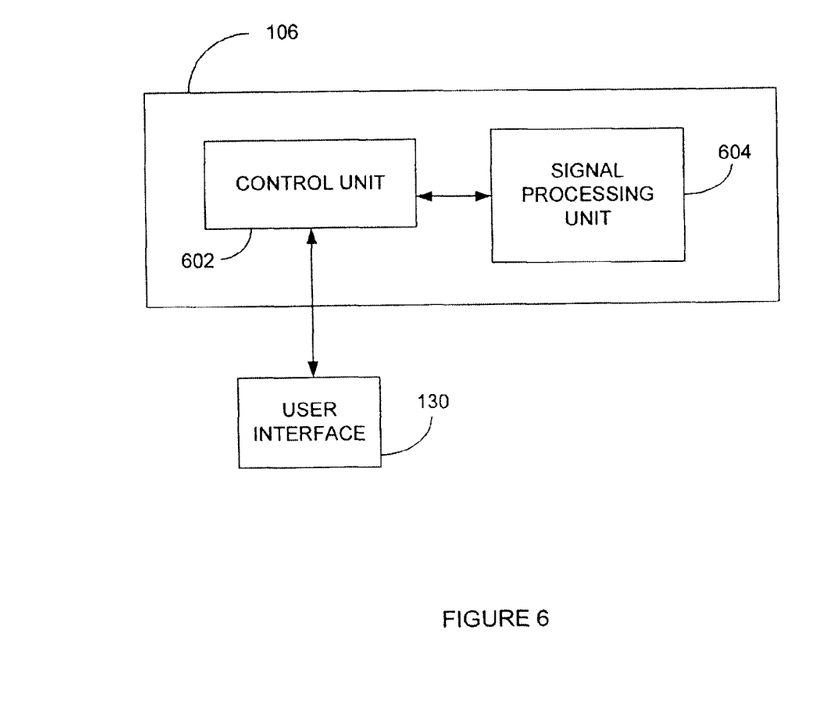
FIG. 6 is a block diagram of an exemplary control module.

FIG. 6 illustrates an exemplary embodiment for the control module 106. The control module 106 may comprise a control unit 602 and a signal processing unit 604. The user interface 130 is in communication with the control unit 602. Additional components may be present but are not illustrated for simplicity, such as a memory, a power supply, signal processing electronics, etc. The control unit 602 may be provided by a combination of hardware and software components, with some components being implemented by a given function or operation of a hardware or software system. For example, it may be implemented using a software application running on a processor, hardwired logic, Field-Programmable Gate Arrays (FPGAs), analog systems, etc. The processor may be any device that can perform operations on data. Examples are a central processing unit (CPU), a microprocessor, and a front-end processor.

The signal processing unit 604 may receive the detection measurements and process the signals. In particular, the detector sensors 404 generate pulses when photons are received. The pulses are counted and then converted into tallies (i.e. counts/time period) by the signal processing unit 604. The time at which the tallies occur is also recorded. This data may then be used by reconstruction software, remotely from the control module 106, to generate a Tomographic image. In some embodiments, further processing of the tallies may be performed directly in the control module 106 such that the Tomographic images are reconstructed locally.

In some embodiments, a rapid scan mode may be provided such that low quality raw data is displayed to the operator during acquisition. In rapid scan mode, the operator may choose a region of inspection and inspect the region at high speed but low statistical quality, to ensure that desired sections or material are being inspected. The statistically poor image may provide enough visual information for a skilled operator to identify the region of inspection. However, the data quality may be insufficient for accurate gauging or material identification through density. In rapid scan mode, acquisition may move from the region closest to the scanning module 104 and progress deeper into the object of interest. As such, the operator can stop acquisition if the region of interest has been completely identified and save time.

With the region of interest known, the operator may switch to a high quality mode over the region of interest and thus provide high quality raw data suitable for tomography, which may also be displayed to the user. The high quality raw data will be used to generate the Tomographic images, either remotely or locally. This process saves time by eliminating the acquisition of more time consuming high quality statistics for areas not of interest for the inspection.

It should be noted that the present invention can be carried out as a method, can be embodied in a system or on a computer readable medium or computer programming product including non-transient machine-readable instructions sets.

Figure 7:
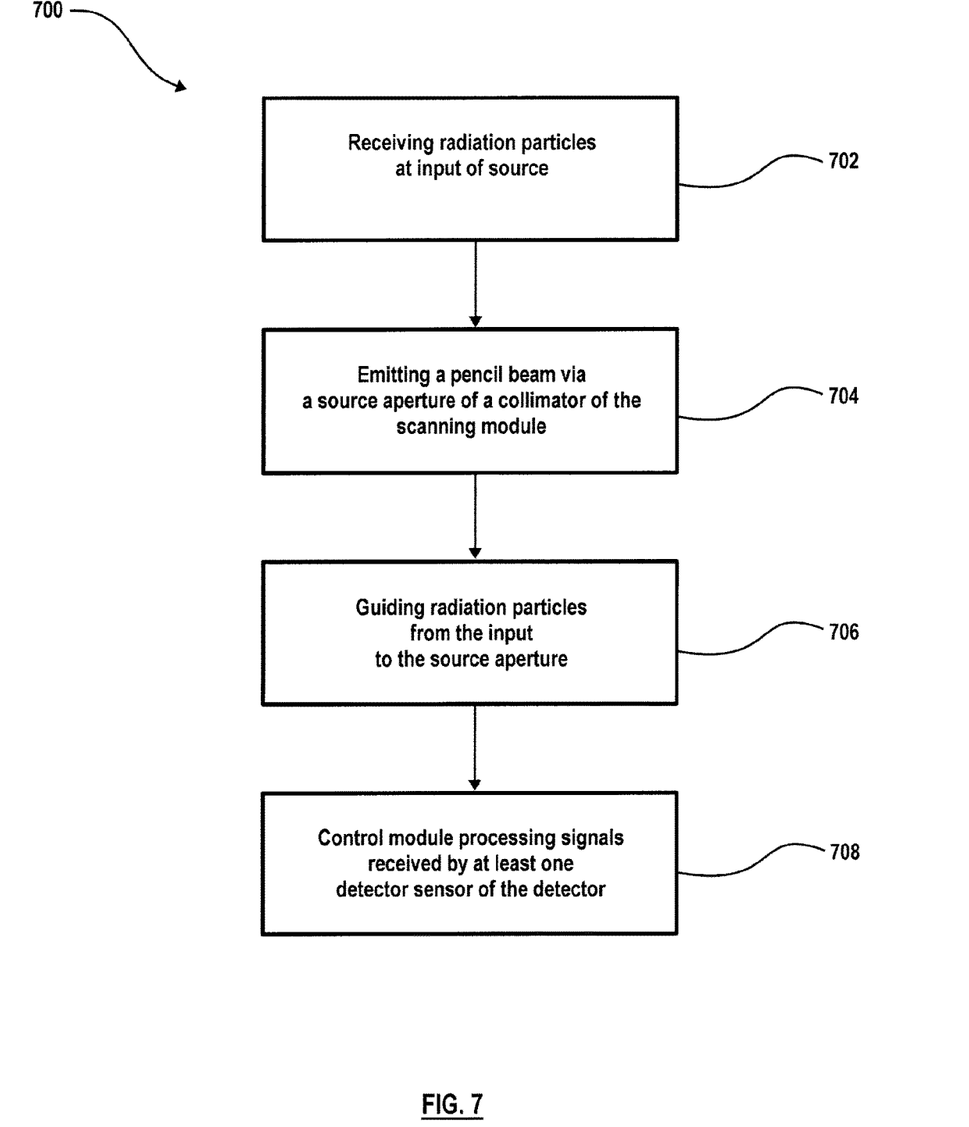
FIG. 7 illustrates an exemplary method in accordance with an aspect of the present invention.

For example, in accordance with one non-limiting exemplary implementation of the present invention, as shown in FIG. 7, there may be provided a method 700 for collecting Tomographic inspection data of objects using Compton scatter radiation using a scanning module comprising a source and a detector. The method may include: at 702, receiving radiation particles at an input of the source; at 704, emitting a pencil beam via a source aperture of a collimator of the scanning module; at 706, guiding the radiation particles from the input to the source aperture at least partly by a source housing of the scanning module, the source housing made of a first shielding material; and at 708, a control module operatively connected to the scanning module processing signals received by at least one detector sensor of the detector, wherein the detector comprises at least one detector slit extending substantially orthogonally to an imaging plane, the at least one detector sensor provided behind each at least one detector slit, and a detector housing made of a second shielding material.

The embodiments of the invention described above are intended to be exemplary only. Thus, changes in the details of construction and combination and arrangement of parts and steps may be made, alterations, modifications and variations can be effected to the particular embodiments by those of skill in the art without departing from the scope of this disclosure, which is defined solely by the claims appended hereto.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances, without departing from the scope of the invention, which is to be limited only by the claims.

The invention claimed is:

1. An apparatus for inspecting an object, the apparatus comprising:
   a scanning module comprising a source and a detector, the source having an input for receiving radiation particles, a collimator comprising a source aperture for emitting a pencil beam, and a source housing made of a first shielding material for guiding the radiation particles from the input to the source aperture, the detector having at least one detector slit extending substantially orthogonally to an imaging plane, at least one detector sensor provided behind each at least one detector slit, and a detector housing made of a second shielding material; and
   a control module operatively connected to the scanning module and configured to operate the source and the detector in the scanning module, and to process signals received by the at least one detector sensor.

2. The apparatus of claim 1, wherein the source housing comprises a primary shield around the collimator and a secondary shield on each side of the primary shield.

3. The apparatus of claim 2, wherein the source housing is symmetric, and the secondary shield on each side of the primary shield extends away from the primary shield and blocks photons with a direct line of sight between the source and the detector.

4. The apparatus of claim 2, wherein the primary shield is rotatable about an axis and the secondary shield is fixed.

5. The apparatus of claim 1, wherein the at least one detector slit comprises a primary slit extending vertically along a front side of the detector, and at least one secondary slit offset from the primary slit and positioned to receive scattered photons from a same point of origin as those received by the primary slit.

6. The apparatus of claim 1, wherein the at least one detector sensor comprises an array of detector sensors behind each at least one detector slit for receiving scattered photons from a same point of origin.

7. The apparatus of claim 1, wherein the at least one detector slit comprises an array of detector slits positioned adjacently for receiving scattered photons from different points of scatter.

8. The apparatus of claim 1, wherein the scanning module comprises a retention system for the source and the detector allowing at least one of relative and coordinated movement.

9. The apparatus of claim 8, wherein the movement is rotational and translational.

10. The apparatus of claim 8, wherein the coordinated movement maintains a fixed rotation angle between the source and the detector and sweeps the source and detector across an inspection area.

11. The apparatus of claim 8, wherein a speed of movement is dynamically adjustable.

12. The apparatus of claim 8, wherein the retention system comprises an overpass mechanism allowing the source to pass at least one of above and beneath the detector.

13. The apparatus of claim 1, wherein the control module comprises a control unit and a signal processing unit, and the signal processing unit displays raw data during acquisition on a user interface.

14. The apparatus of claim 13, wherein the control unit is adapted to receive scanning instructions from the user interface to target a given region of inspection.

15. The apparatus of claim 1, wherein the scanning module and the control module are releasably connected via a cable.

16. An apparatus for inspecting an object, the apparatus comprising:
a scanning module comprising a source and a detector, the source having an input for receiving radiation particles, a collimator comprising a source aperture for emitting a pencil beam, and a source housing made of a first shielding material for guiding the radiation particles from the input to the source aperture, the source housing having a primary shield around the collimator and a secondary shield on each side of the primary shield extending away therefrom, the secondary shield on each side of the primary shield extending away from the primary shield and blocking photons with a direct line of sight between the source and the detector, the detector having at least one detector slit, at least one detector sensor provided behind each at least one detector slit, and a detector housing made of a second shielding material; and
a control module operatively connected to the scanning module and configured to operate the source and detector in the scanning module, and to process signals received by the at least one detector sensor.

17. An apparatus for inspecting an object, the apparatus comprising:
a scanning module comprising a source and a detector, the source having an input for receiving radiation particles, a collimator comprising a source aperture for emitting a pencil beam, and a source housing made of a first shielding material for guiding the radiation particles from the input to the source aperture, the detector having at least one detector slit, at least one detector sensor provided behind each at least one detector slit, and a detector housing made of a second shielding material; and
a control module operatively connected to the scanning module, configured to operate the source and the detector in the scanning module and to process signals received by the at least one detector sensor, and comprising a control unit and a signal processing unit, the signal processing unit adapted to display low quality raw data on a user interface in a rapid scan mode and high quality raw data on the user interface in a high quality mode.

18. An apparatus for inspecting an object, the apparatus comprising:
a scanning module comprising a source and a detector, the source having an input for receiving radiation particles, a collimator comprising a source aperture for emitting a pencil beam, and a source housing made of a first shielding material for guiding the radiation particles from the input to the source aperture, the detector having at least one detector slit, at least one detector sensor provided behind each at least one detector slit, and a detector housing made of a second shielding material; and
a control module operatively connected to the scanning module by a flexible and releasable cable and configured to operate the source and detector in the scanning module, and to process signals received by the at least one detector sensor.

19. A method for collecting Tomographic inspection data of objects using Compton scatter radiation using a scanning module comprising a source and a detector, the method comprising:
receiving radiation particles at an input of the source;
emitting a pencil beam via a source aperture of a collimator of the scanning module;
guiding the radiation particles from the input to the source aperture at least partly by a source housing of the scanning module, the source housing made of a first shielding material; and
using a control module operatively connected to the scanning module, processing signals received by at least one detector sensor of the detector,
wherein the detector comprises at least one detector slit extending substantially orthogonally to an imaging plane, the at least one detector sensor provided behind each at least one detector slit, and a detector housing made of a second shielding material.

* * * * *